(12) United States Patent
Sansoucy

(10) Patent No.: US 11,744,986 B2
(45) Date of Patent: Sep. 5, 2023

(54) CATHETER HAVING AN EXPANDABLE LUMEN AND METHOD OF MANUFACTURE

(71) Applicant: MOZARC MEDICAL US LLC, Minneapolis, MN (US)

(72) Inventor: Michael Sansoucy, Wrentham, MA (US)

(73) Assignee: Mozarc Medical US LLC, Minneapolis, MN (US)

( * ) Notice: Subject to any disclaimer, the term of this patent is extended or adjusted under 35 U.S.C. 154(b) by 1203 days.

(21) Appl. No.: 16/270,678

(22) Filed: Feb. 8, 2019

(65) Prior Publication Data

US 2019/0167946 A1 Jun. 6, 2019

Related U.S. Application Data

(60) Continuation of application No. 14/748,392, filed on Jun. 24, 2015, now Pat. No. 10,238,836, which is a
(Continued)

(51) Int. Cl.
*B29C 48/00* (2019.01)
*B29C 48/11* (2019.01)
(Continued)

(52) U.S. Cl.
CPC .... *A61M 25/0102* (2013.01); *A61M 25/0009* (2013.01); *A61M 25/0026* (2013.01); *A61M 25/09* (2013.01); *B29C 48/001* (2019.02); *B29C 48/10* (2019.02); *B29C 48/11* (2019.02); *B29C 48/12* (2019.02); *B29C 48/15* (2019.02); *B29C 48/21* (2019.02); *B29C 48/91* (2019.02); *B29C 48/912* (2019.02); *B29C 48/9105* (2019.02); *D01D 5/24* (2013.01); *A61M 2025/0024* (2013.01); *A61M 2025/0025* (2013.01);
(Continued)

(58) Field of Classification Search
CPC ............. B29C 48/9105; B29C 48/91; A61M 2025/0025; A61M 2025/0035; A61M 2025/0037; A61M 25/0026; A61M 2025/0024
See application file for complete search history.

(56) References Cited

U.S. PATENT DOCUMENTS 4,174,365 A 11/1979 Pahl
D272,651 S 2/1984 Mahurkar
(Continued)

FOREIGN PATENT DOCUMENTS

EP 0555780 A2 8/1993
WO 9737699 A1 10/1997

OTHER PUBLICATIONS

Prosecution History from U.S. Appl. No. 12/826,795, dated Apr. 2, 2012 to Mar. 24, 2015, 79 pp.
(Continued)

*Primary Examiner* — Xiao S Zhao
*Assistant Examiner* — John J DeRusso
(74) *Attorney, Agent, or Firm* — Shumaker & Sieffert, P.A.

(57) ABSTRACT

A single or multiple lumen catheter is disclosed which includes an expandable lumen. The expandable lumen is movable from a collapsed or sealed configuration to an open or expanded configuration. In the open configuration, the expandable lumen is dimensioned to receive a guidewire or stylet or facilitate the introduction of fluids into a patient.

8 Claims, 5 Drawing Sheets

Related U.S. Application Data division of application No. 12/826,795, filed on Jun. 30, 2010, now abandoned.

(60) Provisional application No. 61/222,561, filed on Jul. 2, 2009.

(51) Int. Cl.
| | |
|---|---|
| *B29C 48/21* | (2019.01) |
| *B29C 48/88* | (2019.01) |
| *B29C 48/91* | (2019.01) |
| *D01D 5/24* | (2006.01) |
| *B29C 48/15* | (2019.01) |
| *B29C 48/10* | (2019.01) |
| *B29L 31/00* | (2006.01) |
| *A61M 25/01* | (2006.01) |
| *A61M 25/09* | (2006.01) |
| *B29C 48/12* | (2019.01) |
| *A61M 25/00* | (2006.01) |

(52) U.S. Cl.
CPC ............ *A61M 2025/0031* (2013.01); *A61M 2025/0035* (2013.01); *A61M 2025/0037* (2013.01); *B29L 2031/7542* (2013.01)

(56) References Cited

U.S. PATENT DOCUMENTS

| | | |
|---|---|---|
| 4,894,057 A | 1/1990 | Howes |
| 5,025,778 A | 6/1991 | Silverstein et al. |
| 5,063,018 A | 11/1991 | Fontirroche et al. |
| 5,167,623 A | 12/1992 | Cianci et al. |
| 5,195,962 A | 3/1993 | Martin et al. |
| 5,197,951 A | 3/1993 | Mahurkar |
| 5,209,723 A | 5/1993 | Twardowski et al. |
| 5,221,255 A | 6/1993 | Mahurkar et al. |
| 5,221,256 A | 6/1993 | Mahurkar |
| 5,273,527 A | 12/1993 | Schatz et al. |
| 5,318,518 A | 6/1994 | Plechinger et al. |
| 5,374,245 A | 12/1994 | Mahurkar |
| 5,378,230 A | 1/1995 | Mahurkar |
| 5,395,316 A | 3/1995 | Martin |
| 5,403,291 A | 4/1995 | Abrahamson |
| 5,405,320 A | 4/1995 | Twardowski et al. |
| 5,451,206 A | 9/1995 | Young |
| 5,464,398 A | 11/1995 | Haindl |
| 5,486,159 A | 1/1996 | Mahurkar |
| 5,509,897 A | 4/1996 | Twardowski et al. |
| 5,569,182 A | 10/1996 | Twardowski et al. |
| 5,630,806 A | 5/1997 | Inagaki et al. |
| 5,685,867 A | 11/1997 | Twardowski et al. |
| 5,902,476 A | 5/1999 | Twardowski |
| 5,961,486 A | 10/1999 | Twardowski |
| 6,126,631 A | 10/2000 | Loggie |
| 6,319,228 B1 | 11/2001 | Kastenhofer |
| 6,540,734 B1 | 4/2003 | Chiu et al. |
| 6,592,565 B2 | 7/2003 | Twardowski |
| 7,048,713 B2 | 5/2006 | Wang |
| 7,141,035 B2 | 11/2006 | Haggstrom |
| 2004/0167478 A1 | 8/2004 | Mooney et al. |
| 2005/0055012 A1 | 3/2005 | Trerotola |
| 2009/0301643 A1 | 12/2009 | Tilson et al. |
| 2011/0004197 A1 | 1/2011 | Sansoucy |
| 2011/0004198 A1 | 1/2011 | Hoch |

OTHER PUBLICATIONS

Prosecution History from U.S. Appl. No. 14/748,392, dated Jun. 25, 2015 to Dec. 5, 2018, 78 pp.

CATHETER HAVING AN EXPANDABLE LUMEN AND METHOD OF MANUFACTURE

CROSS REFERENCE TO RELATED APPLICATIONS

This application is a continuation of U.S. patent application Ser. No. 14/748,392 filed Jun. 24, 2015, which is a divisional of U.S. application Ser. No. 12/826,795, filed Jun. 30, 2010, now abandoned, which claims the benefit of and priority to U.S. Provisional Patent Application Ser. No. 61/222,561, filed Jul. 2, 2009, the entire contents of each of which are incorporated by reference herein.

BACKGROUND

1. Technical Field

The present disclosure relates to a medical catheter and, more particularly, to a medical catheter including an expandable lumen.

2. Background of Related Art

Catheters for supplying and/or withdrawing fluids into and/or from the body are well known in the art. Such catheters may be employed for medication delivery, urine removal, blood treatment, e.g., dialysis, etc. In the area of dialysis, single, double and triple lumen catheters are well known. Typically, double or dual lumen dialysis catheters define an arterial lumen and a venous lumen for simultaneously withdrawing and returning blood from and to the body. A pair of single lumen catheters can be used to achieve the same function. Triple lumen catheters generally include arterial and venous lumens and a guidewire lumen. The guidewire lumen is provided to accommodate a guidewire to facilitate catheter placement within the body and/or facilitate delivery of a medical fluid into the body.

One drawback associated with providing a guidewire lumen within a catheter is that the inclusion of a guidewire lumen effectively reduces the cross-sectional area available to accommodate the remaining lumen or lumens. Thus, the maximum fluid flow rate in the remaining lumen or lumens of the catheter as compared to a catheter not having a guidewire lumen is reduced.

Accordingly, a continuing need exists in the medical arts for a catheter including a guidewire lumen with improved flow rates through the existing lumen or lumens.

SUMMARY

The present disclosure relates to a catheter comprising an elongated body having a proximal end and a distal end and defining at least one lumen. The body includes a longitudinal slit which is expandable from a substantially sealed configuration to an expanded configuration to define an expandable lumen positioned adjacent the at least one lumen. The expandable lumen is dimensioned to receive a guidewire and/or a stylet in the expanded configuration. In one embodiment, the catheter includes a single lumen and the expandable lumen extends longitudinally along an inner wall of the elongated body defining the single lumen.

In one embodiment, the expandable lumen is defined between the inner wall of the elongated body and a resilient membrane. The resilient membrane may be formed integrally with the elongated body. Alternatively, the resilient membrane may be secured to the inner wall of the elongated body using for example, adhesives or welding.

In an alternative embodiment, the at least one lumen includes a first lumen and a second lumen and a longitudinal septum positioned between the first lumen and the second lumen. In this embodiment, the longitudinal slit extends through the septum such that when the longitudinal slit is in the expanded configuration, the expandable lumen extends through the septum. The septum can be positioned substantially along the diameter of the elongated body such that the first lumen and the second lumen are substantially D-shaped. Alternatively, the septum may be positioned to define first and second lumens which have different cross-sectional areas.

The catheter may be formed of a first material having a first coefficient of friction and a second material having a second coefficient of friction which is less than the first coefficient of friction, wherein at least a portion of the elongated body defining the slit is formed of the second material.

The present disclosure also relates to a method of manufacturing a multi-lumen catheter, comprising the following steps:

i) extruding a catheter body having a first lumen and a second lumen and a septum separating the first lumen from the second lumen, the septum including a removable material positioned within and extending along the length of the septum, wherein the septum is extruded from an elastomeric material; and ii) removing the removable material from the septum to define a slit which extends through the septum along the length of the septum, the slit being expandable to define a third lumen.

In one embodiment, the step of removing the removable material from the septum includes pulling the removable material from the septum. In another embodiment, the removable material is a dissolvable or degradable material and the step of removing the removable material from the septum includes exposing the catheter to a solvent to dissolve or degrade the removable material within the septum. This method may also include the step of flushing the third lumen to remove the dissolved/degraded material from the third lumen.

In an alternative method of manufacturing a multi-lumen catheter, the method comprises the following steps:

i) extruding a catheter body having a first lumen, a second lumen, and a third lumen positioned between the first and second lumens and extending through a septum of the catheter body, the catheter body being formed of a first material having a first melting temperature;

ii) providing a layer of a second material on an inner surface of the septum defining the third lumen, the second material having a melting temperature greater than the first material;

iii) directing a fluid through the first and second lumens to move the third lumen to a collapsed configuration;

iv) melting the first material without melting the second material while the third lumen is in the collapsed configuration; and v) cooling the first material to allow the first material to set with the central lumen in the collapsed configuration.

In yet another embodiment of the method of manufacturing a multi-lumen catheter, the method comprises the following steps:

i) extruding a catheter body having a first lumen, a second lumen, and a third lumen positioned between the first and second lumens and extending through a septum of the catheter body, the catheter body being formed of a first material having a first melting temperature;

ii) providing a layer of second material on an inner surface of the catheter body defining the first and second lumens, the second material having a melting temperature lower than the first material;

iii) directing a fluid through the first and second lumens to move the third lumen to a collapsed configuration;

iv) melting the second material without melting the first material while the third lumen is in the collapsed configuration; and v) cooling the second material to allow the second material to set with the central lumen in the collapsed configuration.

In yet another embodiment of the method of manufacturing a multi-lumen catheter, the method comprises the following steps:

i) extruding a catheter body having a first lumen, a second lumen, a septum positioned between the first and second lumens, and a hollow tube extending longitudinally through the septum; and ii) forcing a fluid through the hollow tube to expand the hollow tube. In this embodiment, the extruding step does not include melting the hollow tube. The hollow tube may be formed from a material which has enhanced lubricity as compared to a material forming the septum.

BRIEF DESCRIPTION OF THE DRAWINGS

Various embodiments of the presently disclosed catheter with expandable lumen and methods of manufacturing such a catheter are disclosed herein with reference to the drawings, wherein.

DETAILED DESCRIPTION OF EMBODIMENTS

Figure 1:
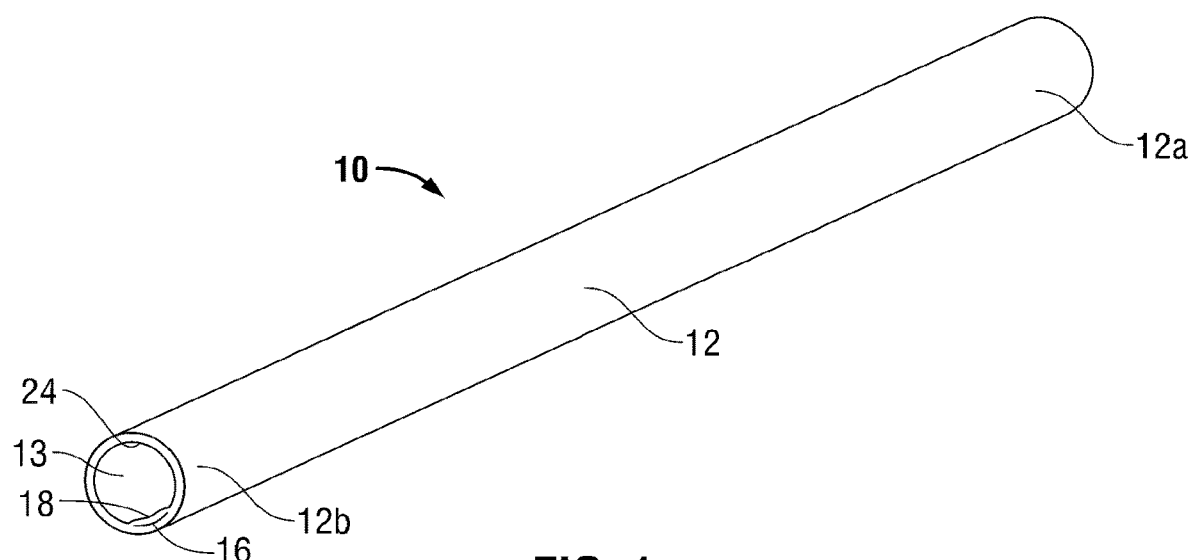
FIG. 1 is a side perspective view of one embodiment of the presently disclosed catheter with expandable lumen.

Embodiments of the presently disclosed catheter having an expandable lumen and methods for manufacturing the catheter will now be described in detail with reference to the drawings wherein like reference numerals designate identical or corresponding elements in each of the several views.

The exemplary embodiments of the catheter disclosed herein are discussed in terms of medical catheters for the administration of fluids (withdrawal or introduction) relative to the body of a subject and, more particularly, in terms of a hemodialysis catheter. However, it is envisioned that the present disclosure may be employed with a range of catheter applications including surgical, diagnostic and related treatments of diseases and body ailments of a subject. It is further envisioned that the principles relating to the catheter disclosed include employment with various catheter related procedures, such as, for example, hemodialysis, cardiac, abdominal, urinary, intestinal, and in chronic and acute applications. Moreover, the catheter can be used for administration of fluids such as, for example, medication, saline, bodily fluids, blood and urine.

In the discussion that follows, the term "proximal" or "trailing" will refer to the portion of a structure that is closer to a clinician, while the term "distal" or "leading" will refer to the portion that is further from the clinician. As used herein, the term "subject" refers to a human patient or other animal. The term "clinician" refers to a doctor, nurse or other care provider and may include support personnel.

Figure 1A:
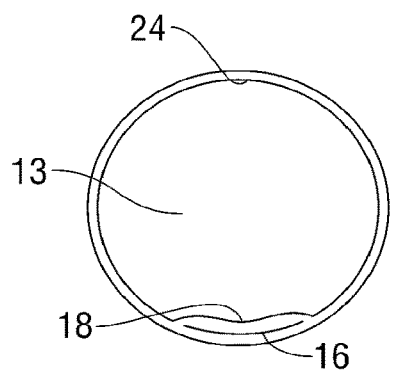
FIG. 1A is a front view from the distal end of the catheter shown in FIG. 1 with the lumen in a sealed configuration.
Figure 2:
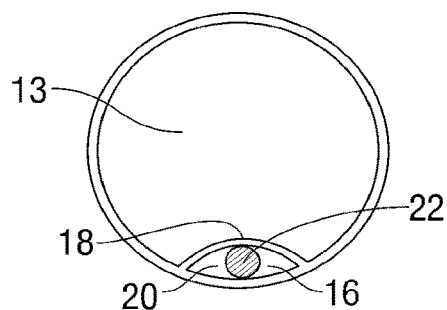
FIG. 2 is a front view from the distal end of the catheter shown in FIG. 1 with the lumen in an expanded configuration and a guidewire extending through the lumen.

FIGS. 1-2 illustrate one embodiment of the presently disclosed catheter with expandable lumen shown generally as 10. Catheter 10 includes an elongated body 12 having a proximal end 12a and a distal end 12b. Elongated body 12 defines a lumen 13 which extends from proximal end 12a of elongated body 12 to the distal end 12b of elongated body 12. A longitudinal slit 16 is defined along the length of body 12 between body 12 and a resilient membrane 18. Membrane 18 can be formed integrally with elongated body 12 or, alternatively, can be formed separately from and secured to body 12 using conventional techniques, e.g., welding, adhesives, etc. Resilient membrane 18 is positioned along body 12 to define an expandable lumen 20 (FIG. 2) which is dimensioned to receive a stylet (FIG. 7) or guidewire 22 (FIG. 2) or facilitate introduction or removal of fluid, e.g., medication, contrasting agent, saline, etc., through the catheter 10. As illustrated in FIG. 1A, in its normal or collapsed configuration, membrane 18 is positioned adjacent an inner wall 24 of catheter 10. Thus, when membrane 18 is in its collapsed configuration, substantially the full diameter of lumen 14 is available for fluid flow and the fluid flow rate at a given pressure for a catheter having a specified diameter can be maximized.

Figure 3:
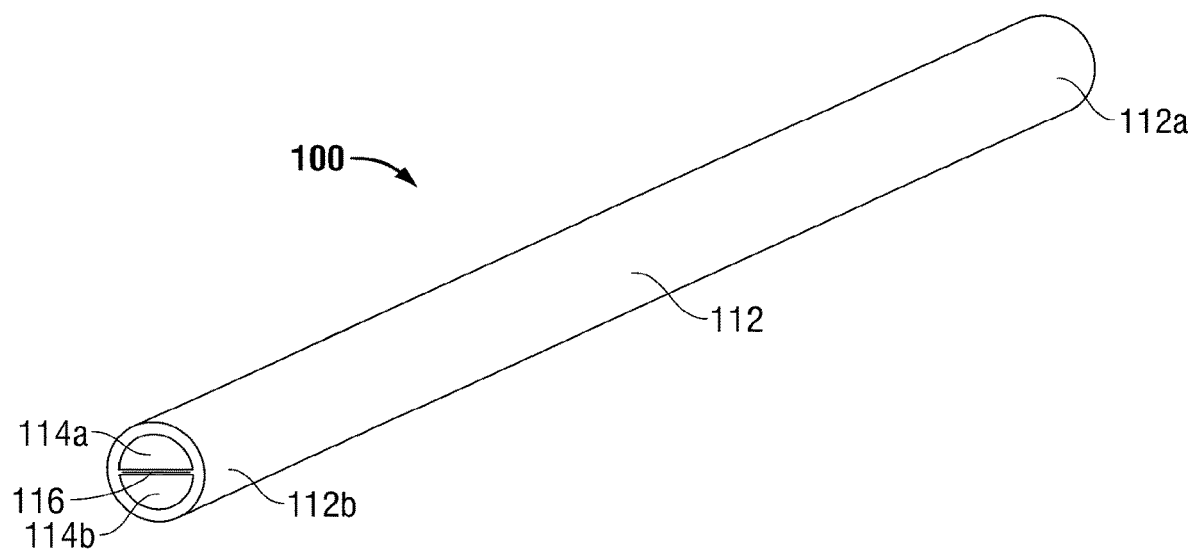
FIG. 3 is a side perspective view from the distal end of another embodiment of the presently disclosed catheter with expandable lumen.
Figure 4:
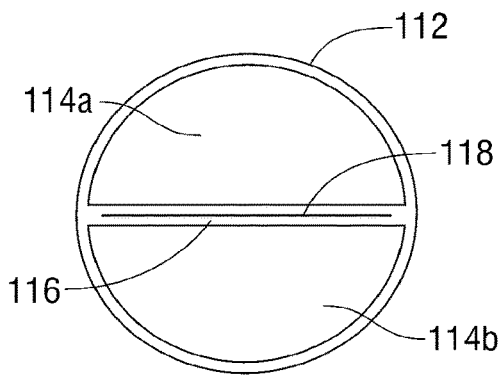
FIG. 4 is a front view of the distal end of the catheter shown in FIG. 3 with the expandable lumen in a sealed configuration.
Figure 5:
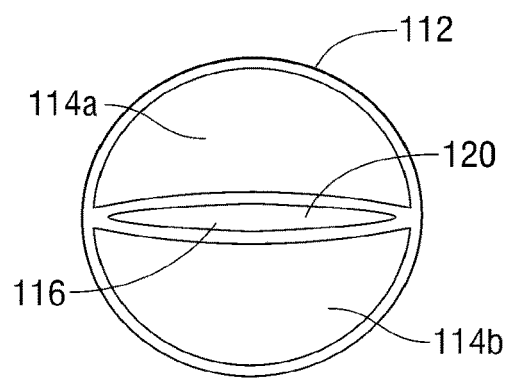
FIG. 5 is a front view of the distal end of the catheter shown in FIG. 4 with the expandable lumen in an expanded configuration.

FIGS. 3-5 illustrate another embodiment of the presently disclosed catheter with expandable lumen shown generally as 100. Catheter 100 includes an elongated body 112 having a proximal end 112a and a distal end 112b. A pair of lumens 114a and 114b extend from the proximal end 112a to the distal end 112b of body 112. A septum 116 extends along the length of elongated body 112 between lumens 114a and 114b. Although septum 116 is illustrated as being positioned along the diameter of body 112 to define two lumens of substantially equal cross-sectional area, it is envisioned that the septum 116 can be positioned to define two lumens of unequal cross-sectional areas.

Catheter 100 may be made of any suitable material. In certain embodiments, catheter 10 is formed of polyurethane, such as an aliphatic or aromatic polyurethane. However, catheter 100 may be made of any suitable polymer such as thermoplastic, polyolefin, fluoropolymer (such as fluorinated ethylene propylene ("FEP"), polytetrafluoroethylene PEFE, perfluoroalkoxy ("PFA") polyvinylidene fluoride (PVDF)), polyvinyl chlorideneoprene PVC, silicone elastomer of fluoroelasatomers (such as copolymers of hexafluoropropylene (HFP) and vinylidene fluoride (VDF or VF2), terpolymers of tetrafluoroethylene (TFE), vinylidene fluoride (VDF) and hexafluoropropylene (HFP), and perfluoromethylvinylether (PMVE)).

Referring particularly to FIGS. 4 and 5, a slit 118 is defined along the length of septum 116. Septum 116 is formed of an elastomeric material, such that the slit is expandable from a closed or substantially closed or collapsed configuration (FIG. 4) to an expanded or open configuration (FIG. 5). In the expanded or open configuration, the slit 118 defines a third lumen 120 which can be dimensioned to receive a guidewire 225 (FIG. 6) or to facilitate introduction or removal of fluid, e.g., medication, contrasting agent, saline, etc. into a patient.

Figure 6:
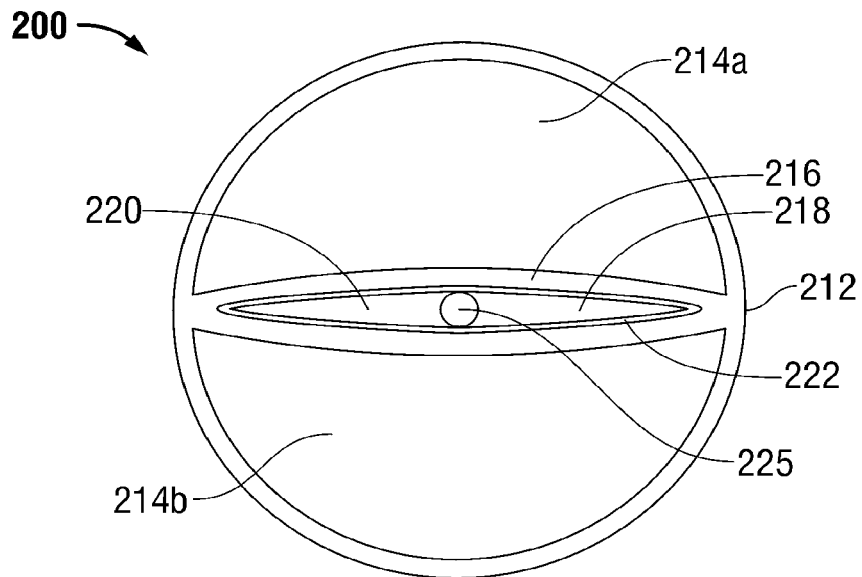
FIG. 6 is a front view of another embodiment of the presently disclosed catheter with expandable lumen with the lumen in an expanded configuration and a guidewire positioned within the lumen.
Figure 7:
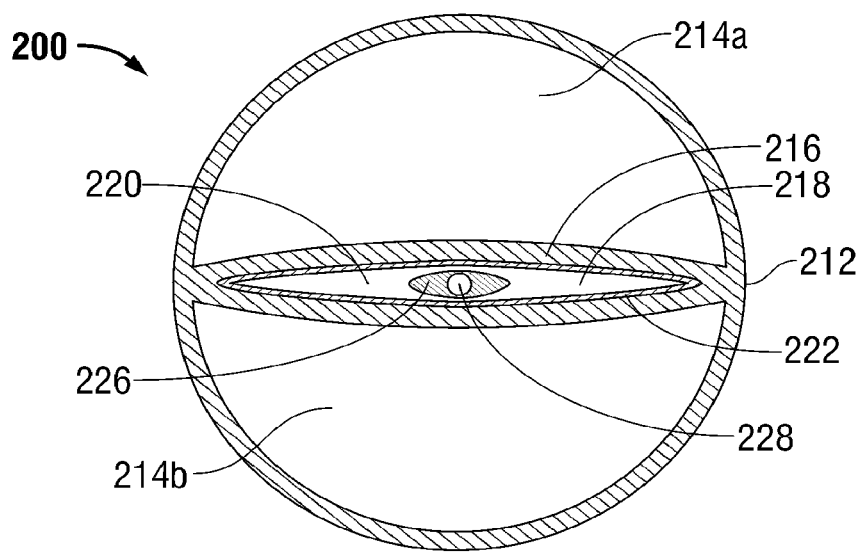
FIG. 7 is a cross-sectional view of the catheter shown in FIG. 6 with the lumen in an expanded configuration and a stylet positioned within the lumen.

FIGS. 6 and 7 illustrate front and cross-sectional views of another embodiment of the presently disclosed catheter shown generally as 200. Catheter 200 is substantially similar to catheter 100 and includes an elongated body 212 including a septum 216 defining a pair of lumens 214a and 214b. Septum 216 includes an expandable slit 218 which is expandable from a closed configuration (not shown) to an open or expanded configuration (FIGS. 6 and 7) to define a third lumen 220. Catheter 200 differs from catheter 100 in that at least a portion of septum 216 defining slit 218 of catheter 200 is formed of a second material different from the material used to form catheter 200. More specifically, although it is desirable to form elongated body 212 from a soft elastomeric material, the coefficient of friction associated with soft elastomeric materials may render guidewire or stylet insertion through the expandable slit 218 difficult. As such, septum 216 or at least a portion of septum 216 defining the slit 218 can be formed of a second material having a lower coefficient of friction than the elongated body 212 of catheter 200. In one embodiment, the slit 218 is defined by a layer, liner or coating 222 of the second material having a lower coefficient of friction than the body 212 of the catheter 200. Alternatively, the entire septum 216 or portions of septum 216 can be formed of the second material. Yet further, during an extrusion process used to form the body 212, a layer, liner or coating 222 can be employed having a higher melting temperature than the material used to form body 212, thereby ensuring the slit 218 does not adhere to itself, such as by melting, during the manufacturing process.

As illustrated in FIGS. 6 and 7, slit 218 can be dimensioned to receive a guidewire 225 (FIG. 6) and/or a stylet 226 (FIG. 7) when slit 218 is in its expanded or open configuration. Stylet 226 may include a guidewire lumen 228 and may be formed of a material having a low coefficient of friction to facilitate stylet insertion through the slit 218.

Figure 8:
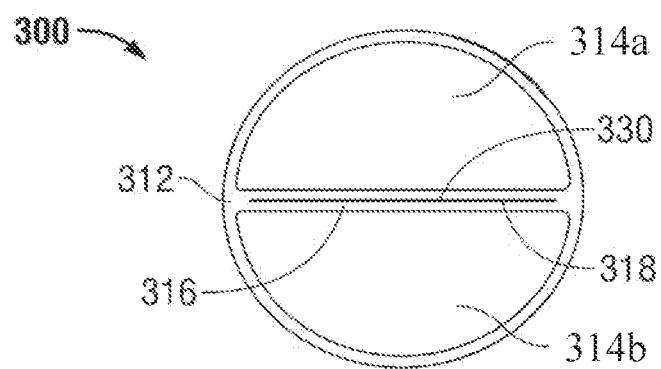
FIG. 8 is a front view of an extruded catheter body, during a first manufacturing process, having a removable material positioned through a septum of the catheter body.

A catheter having a septum including an expandable slit 216, or third lumen 120, can be manufactured in a variety of different ways. Referring to FIG. 8, in one presently disclosed embodiment, catheter body 312 of catheter 300 is extruded of a first material, e.g., silicone, polyurethane, or other soft polymeric material, with a second removable material 330 positioned within the septum 316 to define the slit 318. (Extrusion is a manufacturing process known in the art in which a material is forced through an orifice of a die to form an object having a desired cross-section). The extruded catheter body 312 defines a first lumen 314a and a second lumen 314b. For example, in one embodiment, the removable material 330 can be tailored to neck-down or shrink when a tensile force is applied, wherein a tensile force applied to the removable material 330 can be effective in removing the removable material 330 from the catheter body 312 and forming the slit 318. In yet another embodiment, after catheter body 312 is extruded, catheter body 312 can be exposed to a solvent capable of swelling the first material in which the catheter body 312 is constructed, such as by a dipping process, to effect swelling of the catheter body 312. Thereafter, removable material 330 is pulled from septum 316 to provide a slit through septum 316. Most flexible polymer materials neck-down or shrink when a tensile force is applied and therefore could be used in the application described above. To be even more specific, polymers such as polyurethanes, polyethylenes, polypropylenes, polyvinylchlorides, polyacetal, and so forth, as well as combinations comprising multiple polymer systems or blends can be employed. Also, to one skilled in the art, it is to be apparent that the specific solvent, or chemical employed to induce swelling to the catheter body 312 can be numerous and should be suited to the specific polymer employed such that a majority of the physical properties are retained once the solvent has evaporated from the catheter. In one specific example, isopropyl alcohol can be employed to swell an aliphatic polyurethane sufficiently to pull out removable material 330.

Referring again to FIG. 8, alternatively, the second removable material 330 may include a degradable/dissolvable material positioned within septum 316 to define slit 318. The degradable/dissolvable material 330 can be a starch based material or other known degradable or dissolvable material. After the extrusion process, catheter 300 can be exposed to a solvent which causes the degrading or dissolving of the material 330 to define slit 318. After exposure to the solvent, the expandable lumen defined by slit 318 can be flushed to remove the degraded or dissolved material from the expandable lumen.

Figure 9:
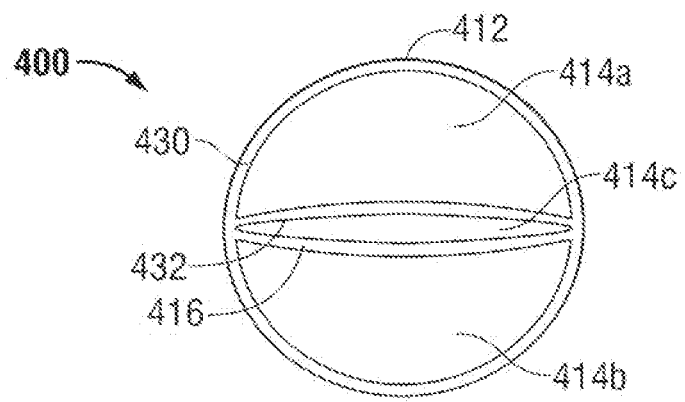
FIG. 9 is a front view of an extruded catheter body, during an alternative manufacturing process, with the expandable lumen extruded in an expanded configuration in the septum to define a lumen through the septum.
Figure 10:
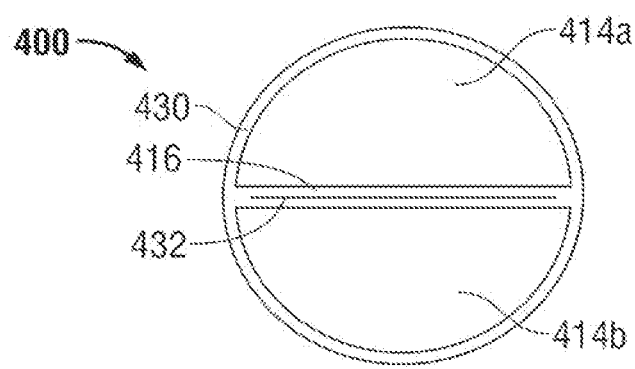
FIG. 10 is a front view of the extruded catheter body shown in FIG. 9 after the expandable lumen has been collapsed and the catheter has been heated to retain the collapsed configuration of the expandable lumen.

Referring to FIGS. 9 and 10, in another embodiment of the presently disclosed manufacturing process, catheter body 412 of catheter 400 is extruded from a first material 430 with three district lumens 414a, 414b and 414c, wherein central lumen 414c (FIG. 9) is defined through septum 416 (FIG. 9). A thin layer of a second material 432 having a higher melting temperature than the first material is provided within septum 416 to define central lumen 414c. Second material 432 can be provided on the inner surface of septum 416 during the extrusion process or, alternatively, after the extrusion process. Next, catheter 400 is positioned within an outer mold and a heated fluid (air, liquid) is forced through lumens 414a and 414b at equal pressure such that the area of the central lumen 414c is decreased, i.e., the central lumen 414c collapses (FIG. 10). The first material is then melted using the heated fluid or other heat source at a temperature which will not melt or render the second material tacky. Thereafter, the first material is cooled to allow the first material to set with the central lumen 414c having a decreased area or collapsed configuration (FIG. 10).

Figure 11:
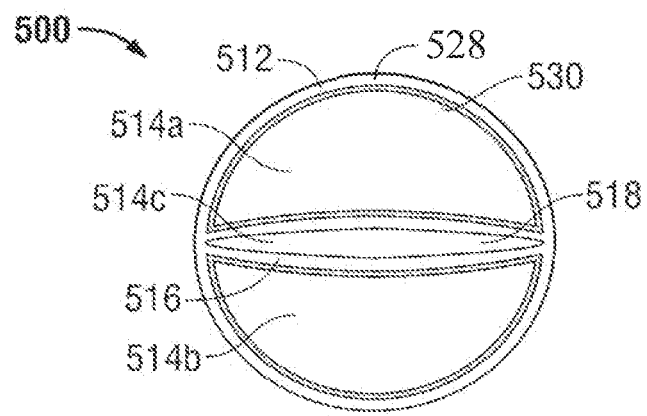
FIG. 11 is a front view of an extruded catheter body during another alternative manufacturing process with the expandable lumen in an expanded configuration and a second material positioned on inner walls of the catheter body defining first and second lumens of the catheter body.
Figure 12:
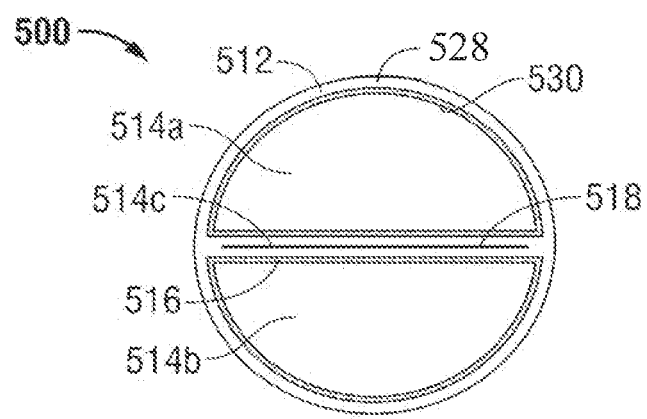
FIG. 12 is a front view of the catheter body shown in FIG. 11 after the expandable lumen has been collapsed during the manufacturing process and the second material has been heated and cooled to retain the expandable lumen in the collapsed configuration.

In yet another embodiment of the presently disclosed manufacturing process, shown in FIGS. 11 and 12, catheter body 512 of catheter 500 is extruded with a first material 528 defining catheter body 512 and a second material 530 covering the inner walls of body 512 defining first and second lumens 514a and 514b. The second material 530 is selected to have a melting temperature lower than the first material 528. A central lumen 514c of catheter body 512 is extruded in an expanded orientation. The extruded catheter 500 (FIG. 11) is placed in an outer mold (not shown) and a heated fluid is forced through lumens 514a and 514b of body 512 to collapse central lumen 514c to define slit 518. The catheter 500 is then heated above the melting temperature of the second material 530 but below the melting temperature of the first material 528. A fluid can be used to collapse slit 518 and a second heating technique can be used to heat the second material 530 above its melting temperature. Alternatively, the fluid can be used to both collapse and heat the catheter body 512. Thereafter, the second material 530 is cooled and allowed to set to provide a catheter body 512 having a closed or collapsed slit 518 (FIG. 12).

Figure 13:
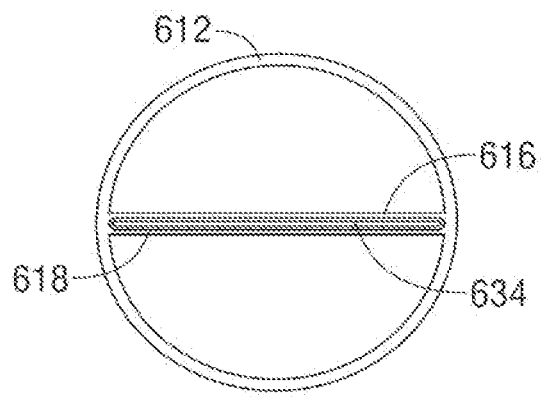
FIG. 13 is a front view of a catheter body having first and second lumens and an expandable central lumen which is coated with a material of enhanced lubricity.

Referring to FIG. 13, an additional step can be performed with respect to each of the above-identified processes to provide enhanced lubricity or ease of manufacture to the central lumen. More specifically, inner walls of septum 616 defining central lumen or slit 618 can be covered with a third material having a low coefficient of friction or enhanced lubricity or differing physical or thermal properties (e.g., higher melting temperature). In one embodiment, the catheter body 612 is extruded with a hollow tube 634 positioned within a die (not shown) to define slit 618 through septum 616. Hollow tube 634 is not melted during the extrusion process such that a liquid can be forced through hollow tube 634 to open slit 618. Hollow tube 634 can be formed from polyethylene terephtalate (PET), polybutylene terephtalate (PBT), FEP, PTFE, or other polymer which will not become tacky or melt at the temperatures reached by the polymer melt employed to form the catheter body 612.

Although specific features of the disclosure are shown in some drawings and not in others, this is for convenience only as each feature may be combined with any or all of the other features in accordance with the disclosure.

It will be understood that various modifications may be made to the embodiments disclosed herein. For example, the various manufacturing processes disclosed to manufacture dual lumen catheters with expandable lumens may also be used to form a single lumen catheter with an expandable lumen where applicable. Therefore, the above description should not be construed as limiting, but merely as exemplifications of embodiments. Those skilled in the art will envision other modifications within the scope and spirit of the claims appended hereto.

The invention claimed is:

1. A method of manufacturing a multi-lumen catheter, the method comprising:
    extruding a catheter body having a first lumen and at least one additional lumen, the catheter body being formed of a first material having a first melting temperature;
    providing a second material on an inner surface of the first lumen, the second material having a melting temperature greater than the first material;
    directing a fluid through the at least one additional lumen to move the first lumen to a collapsed configuration;
    melting the first material without melting the second material while the first lumen is in the collapsed configuration; and
    cooling the first material to allow the first material to set with the first lumen in the collapsed configuration,
    wherein after cooling the first material, the first lumen is configured to receive a guidewire, and
    wherein to receive the guidewire, the first lumen is configured to expand.

2. The method according to claim 1, wherein the at least one additional lumen includes second and third lumens.

3. The method according to claim 2, wherein extruding the catheter body includes providing a septum between the second and third lumens, the first lumen extending through the septum.

4. The method according to claim 1, wherein when the first lumen expands to receive the guidewire, a cross-sectional area of the first lumen is increased.

5. The method according to claim 1, wherein when the first lumen is moved to the collapsed configuration, a cross-sectional area of the first lumen is decreased.

6. The method according to claim 1, wherein providing the second material on the inner surface of the first lumen comprises providing a layer of the second material on the inner surface of the first lumen.

7. The method according to claim 1, wherein in the collapsed configuration, the first lumen is substantially sealed.

8. The method according to claim 1, wherein when the first lumen receives the guidewire, a cross-sectional area of the at least one additional lumen is decreased.

* * * * *